United States Patent [19]

Meserve

[11] Plant 4,996

[45] Mar. 15, 1983

[54] ILEX PLANT—MESCHICK VARIETY

[75] Inventor: Kathleen K. Meserve, St. James, N.Y.

[73] Assignee: The Conard-Pyle Company, West Grove, Pa.

[21] Appl. No.: 277,331

[22] Filed: Jun. 25, 1981

[51] Int. Cl.[3] ..... A01H 5/00

[52] U.S. Cl. ..... Plt./65

[58] Field of Search ..... Plt./65

*Primary Examiner*—James R. Feyrer

*Attorney, Agent, or Firm*—Burns, Doane, Swecker & Mathis

[57] ABSTRACT

A new and distinct variety of Ilex which originated as a cross-pollination of *Ilex aquifolium* and *Ilex pernyi* is provided. The new variety is a quick grower, possesses jagged deep green foliage, produces scarlet berries, exhibits a compact and acutely pyramidal growth habit and good tolerance to cold and heat, and is outstanding for growing as an accent plant.

2 Drawing Figures

SUMMARY OF THE INVENTION

My invention relates to a new, distinctive and useful form of Ilex which was originated by me by crossing at St. James, L.I., N.Y., an unnamed and unpatented seedling of the species known botanically as *Ilex aquifolium* with an unnamed and unpatented seedling of the species known botanically as *Ilex pernyi.*

The object of my breeding was to create a hardy, vigorous and versatile shrub of attractive appearance and unique plant habit which combines the beauty of *Ilex aquifolium* with the dramatic plant habit and interesting foliage of *Ilex pernyi.* This objective was successfully achieved, and the new variety exhibits a combination of characteristics which distinguish it from all offspring resulting from the same cross of which I am aware, as well as all other forms of Ilex of which I am aware.

The following combination of characteristics is exhibited by the new variety:

(a) a vigorous, dense and attractive upright pyramidal evergreen shrub, (b) dull, scarlet fruit which is produced in good quantity in the spring and which attains its full scarlet coloration in mid to late fall, lasting on the bush into late winter or early spring of the following year, (c) cold tolerance which is superior to varieties of *Ilex aquifolium* and equal to, if not superior to varieties of the *Ilex pernyi* as evidenced by the fact that the new variety has survived with little to no visible damage temperatures of −15° F. with winds of over 30 miles per hour, (d) foliage which is primarily ovate-quadrangular in shape and less glossy in appearance than that of *Ilex aquifolium* and which is smaller and much more jagged than such species, and which is approximately 50 percent larger and more jagged than that of *Ilex pernyi,* and (e) a striking plant growth habit which is characterized by forming a symmetrical narrow pyramid to a much greater degree than either of its parents and other seedlings of this cross.

Asexual reproduction by cuttings of my new variety has been accomplished at St. James, L.I., N.Y., and at West Grove, Pa. Succeeding propagations have shown the unique combination of characteristics is fully established and is transmitted to successive generations.

The new variety has been named the Meschick variety.

BRIEF DESCRIPTION OF THE PHOTOGRAPHS

The accompanying photographs show typical specimens of my new variety of Ilex during early May as depicted in color as true as is reasonably possible to make the same in color photographs of this character. The specimens illustrated were being grown in the ground at West Grove, Pa.

DETAILED DESCRIPTION

Figure 1:
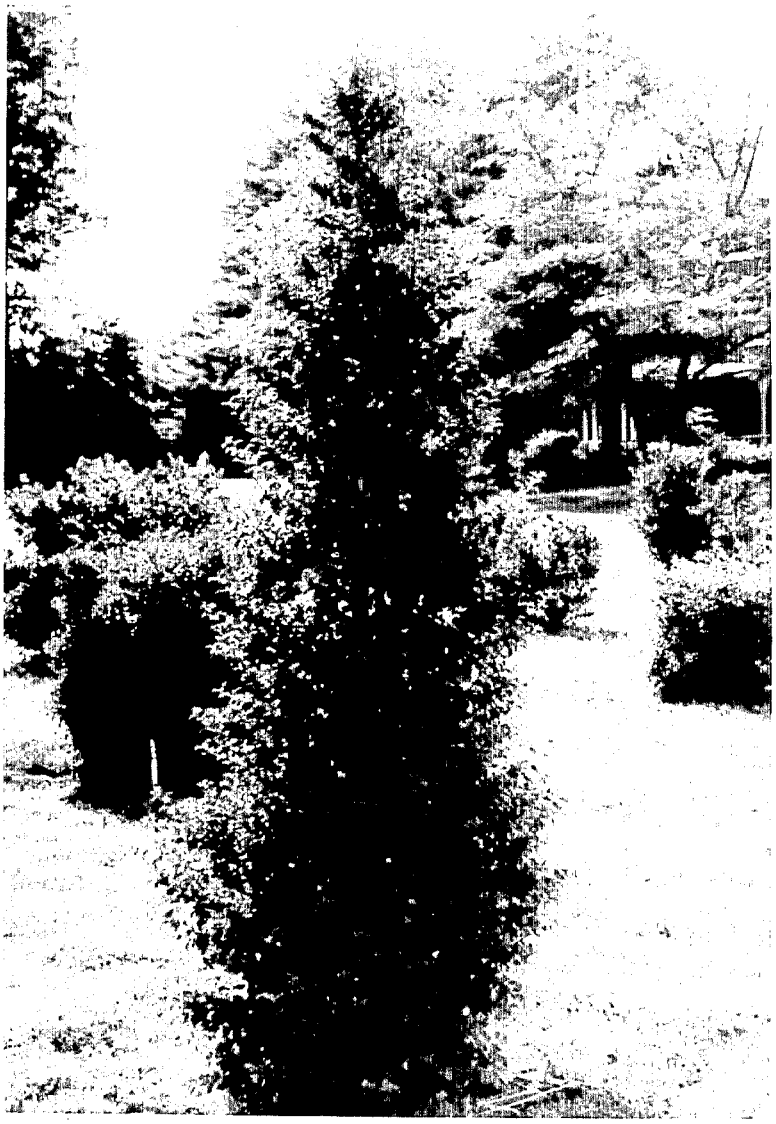
FIG. 1 illustrates the pyrimidal growth habit of the new variety.
Figure 2:
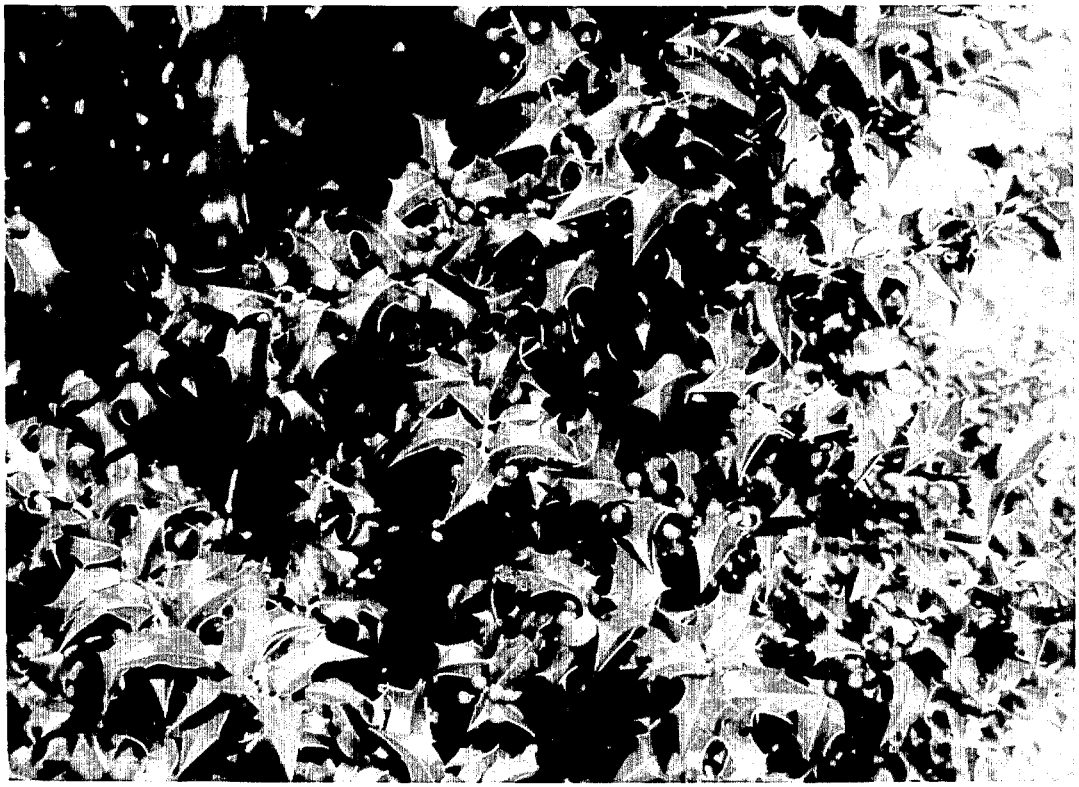
FIG. 2 illustrates typical foliage of the new variety.

The following is a detailed description of my new variety made from the observation of eight year old plants growing in the ground at West Grove, Pa. Color terminology is in accordance with the R.H.S. Colour Chart of The Royal Horticultural Society, London, England.

Class: *Ilex*×*aquipernyi.*

Parentage: *Ilex pernyi*×*Ilex aquifolium.*

Foliage:

*Type.*—Evergreen. Leaves primarily ovate-quadrangular in shape, with a few leaves simply ovate. Apex acute, base obtuse. Margins serrate with from 4 to 6 prominent spines and a single spine at the apex.

*Size.*—Mature leaves on main stem (measurements to tips of spines) — length from approximately 2.9 cm. to 5.1 cm., with an average of approximately 4.1 cm.; width from approximately 1.6 cm. to 3.5 cm., with an average of approximately 2.8 cm. Petiole length from approximately 0.3 cm. to 0.5 cm. Internode length from approximately 1.1 cm. to 1.4 cm.

*Color.*—Mature leaves, upper surface — closest to but slightly greener than Green Group 136A; under surface — Green Group 143A to 143B. Leaves are semi-glossy to glossy.

Rate of growth: Average height and breadth of mature two year old plants is approximately 18 to 24 inches and approximately 10 to 12 inches respectively.

Fruit:

*Color.*—Dull to semi-glossy, Red Group 44A.

*Size.*—Uniform, approximately 0.8 cm.

Stems:

*Color.*—Green Group 143B. The green growth of the young stems may include a purplish cast which tends to disappear as the stems mature.

Plant growth characteristics: Eight year old plants in the landscape averaged approximately 3 feet in breadth at the base, approximately 1.5 feet in breadth at the top, and approximately 9 to 10 feet in height. Most specimens have 2 or 3 main trunks.

I claim:

1. A new and distinct variety of Ilex, substantially as herein shown and described, characterized particularly as to novelty by the unique combination of:

(a) a vigorous, dense and attractive upright pyramidal evergreen shrub, (b) dull, scarlet fruit which is produced in good quantity in the spring and which attains its full scarlet coloration in mid to late fall, lasting on the bush into late winter or early spring of the following year, (c) cold tolerance which is superior to varieties of *Ilex aquifolium* and equal to, if not superior to varieties of *Ilex pernyi* as evidenced by the fact that the new variety has survived with little to no visible damage temperatures of −15° F. with winds of over 30 miles per hour, (d) foliage which is primarily ovate-quadrangular in shape and less glossy in appearance than that of *Ilex aquifolium* and which is smaller and much more jagged than such species, and which is approximately 50 percent larger and more jagged than that of *Ilex pernyi,* and (e) a striking plant growth habit which is characterized by forming a symmetrical narrow pyramid to a much greater degree than either of its parents and other seedlings of this cross.

* * * * *